United States Patent [19]

Takahashi et al.

[11] Patent Number: 5,004,567
[45] Date of Patent: Apr. 2, 1991

[54] PROCESS FOR PRODUCING FLUORINE-CONTAINING ALIPHATIC CARBOXYLIC ACIDS

[75] Inventors: Mitsuru Takahashi; Hideo Shuyama; Osamu Miyano; Yukihiro Tsutsumi, all of Yamaguchi, Japan

[73] Assignee: Tosoh Corporation, Yamaguchi, Japan

[21] Appl. No.: 222,302

[22] Filed: Jul. 22, 1988

Related U.S. Application Data

[63] Continuation of Ser. No. 110,017, May 27, 1986, abandoned, which is a continuation of Ser. No. 866,839, Oct. 13, 1987, abandoned.

[30] Foreign Application Priority Data

| May 27, 1985 | [JP] | Japan | 60-112219 |
| Nov. 29, 1985 | [JP] | Japan | 60-269078 |
| Dec. 27, 1985 | [JP] | Japan | 60-292438 |

[51] Int. Cl.$^5$ .................. C07C 51/15; C11C 3/00
[52] U.S. Cl. ...................... 260/408; 502/551; 502/596
[58] Field of Search .............. 562/551, 596; 260/408

[56] References Cited

U.S. PATENT DOCUMENTS

| 4,098,806 | 7/1978 | Commeyras et al. | 260/408 |
| 4,221,734 | 9/1980 | Commeyras et al. | 260/408 |
| 4,404,398 | 9/1983 | DeLue | 562/551 |
| 4,478,760 | 10/1984 | Blancou et al. | 260/408 |
| 4,578,222 | 3/1986 | Ishikawa et al. | 562/550 |
| 4,759,881 | 7/1988 | Lang et al. | 562/551 |

FOREIGN PATENT DOCUMENTS

| 2555630 | 6/1976 | Fed. Rep. of Germany | 562/550 |
| 2848197 | 5/1980 | Fed. Rep. of Germany | . |
| 2708751 | 11/1980 | Fed. Rep. of Germany | . |
| 2374287 | 7/1978 | France | . |
| 1539300 | 1/1979 | United Kingdom | . |
| 1581891 | 12/1980 | United Kingdom | . |

Primary Examiner—J. E. Evans
Attorney, Agent, or Firm—Sughrue, Mion, Zinn Macpeak & Seas

[57] ABSTRACT

Process for producing fluorine-containing aliphatic carboxylic acids having the general formula of Y—R$_f$—Y' as defined herein by reaction of fluorine-containing aliphatic halogen compounds having the general formula of X—R$_4$—X' as defined herein with carbon dioxide under the presence of zinc in an organic solvent and hydrolysis of the reaction product, wherein the improvement comprises controlling the concentration of carbon dioxide in the organic solvent at a level of 0.3 to 5 mol/l.

1 Claim, No Drawings

PROCESS FOR PRODUCING FLUORINE-CONTAINING ALIPHATIC CARBOXYLIC ACIDS

This is a continuation of application Ser. No. 110,017 filed May 27, 1986, which is a continuation of application Ser. No. 866,839 filed Oct. 13, 1987, both abandoned.

BACKGROUND OF THE INVENTION

1. Field of the Invention

The present invention relates to a process for producing fluorine-containing aliphatic carboxylic acids. More particularly, this invention provides a convenient and effective process for producing the mentioned acids from fluorine-containing aliphatic halogen compounds as starting material. Fluorine-containing aliphatic carboxylic mono- and di-carboxylic acids are useful from their chemical and physiological properties particularly as surfactant, water and oil repellent agent, medicine, agricultural chemical, and the synthetic intermediates thereof. Furthermore, they are useful materials for industrial applications as monomer for producing fluorine-containing polymers of various kinds, such as, for example, for paint materials and for resists employed in the production of LSI's, etc.

2. Description of Prior Arts

Conventional processes of synthesizing fluorine-containing aliphatic carboxylic acids are roughly classified into two groups. One group involves the electrolytic fluorination of aliphatic halogen compounds, and the other starts from a fluorine-containing aliphatic halogen compound.

Among them, processes which utilize the reaction of fluorine-containing aliphatic halogen compounds with carbon dioxide in the presence of metal is known to be relatively readily accessible. They include processes using lithium or magnesium as disclosed in J. Am. Chem. Soc., 73, 3158 (1951); J. Fluorine Chem., 4, 247 (1974); J. Org. Chem., 33, 280 (1967) and Chem. Abs., 53, 6987g: also included is a process which employs zinc alone or a metal couple of zinc and other metal as described in Japanese Laid-Open Patent Application No. Sho 53-77008. Further, a process has been proposed in which the reaction is carried out with zinc powder under the influence of ultrasonic wave. Furthermore, a process in which a fluorine-containing aliphatic halogen compound is made to react with carbon monoxide in the presence of palladium.

However, these processes mentioned above do not suffice to be satisfactorily employed in industry. In the process using magnesium or lithium, the fluorine-containing organic compound produced as intermediate is very unstable and therefore the reaction should be carried out at a low temperature, say $-100°$ or $-40°$ C., and the carboxylic acid can be obtained only with a low yield.

With the processes using zinc metal, a very low yield is expected when zinc is used alone. When zinc is used together with another metal to form a metal couple, the conversion rate of the raw material as well as the yield of carboxylic acid aimed at are improved, but the yield itself is still too low to attain an efficient process for commercial production. In addition, the metal couple of zinc and other metal should be prepared in advance, and it is difficult to operate the process with a high reproducibility and therefore a constant reproducible yield is difficult to obtain.

With the process in which ultrasonic wave is irradiated in the presence of zinc powder, a high power ultrasonic wave generator is difficult to obtain and a low yield is expected. Therefore it is not an effective process from the point of industrial processes. In the process which involves carbon monoxide using palladium as catalyst, the expense of palladium catalyst and the high toxicity of carbon monoxide prevent the process from being advantageously used as an industrial synthetic method.

As has been mentioned above, the conventional processes directed to the production of fluorine-containing aliphatic carboxylic acids starting from fluorine-containing aliphatic halogen compounds suffer from the following problems:

(1) reaction conditions are difficult to set up;
(2) yield is low; and
(3) reaction is complicated to operate.

SUMMARY OF THE INVENTION

The present invention has its object in dissolving these problems. More particularly, this invention intends to provide a process in which fluorine-containing aliphatic carboxylic acids can be produced from fluorine-containing aliphatic halogen compounds used as starting material under a mild condition in a simple and convenient operation and with a high yield.

To overcome difficulties of the prior art processes, the present inventors intended to raise the efficiency in the production of fluorine-containing aliphatic carboxylic acids by the reaction of fluorine-containing aliphatic halogen compound with carbon dioxide in the presence of zinc. Through our intensive investigations we found that the yield of the product is largely influenced by the concentration of carbon dioxide in the reaction system, and at last reached the completion of the present invention.

In the reaction of a fluorine-containing aliphatic halogen compound with carbon dioxide in the presence of zinc, it is generally considered that a reaction intermediate is produced at first which then reacts with carbon dioxide to form a zinc salt of the fluorine-containing aliphatic carboxylic acid. In case the reaction intermediate is unstable, competition arises with side reactions of the possible decomposition reactions, thus leading to a lowered selection rate of the carboxylic acid aimed at. Therefore, an increased concentration of one of the reactants, carbon dioxide, is considered to be effective to raise the selection rate for the carboxylic acid aimed at, though the conversion rate of the raw material can not be increased. With this consideration in mind, correlation between the yield and the concentration of carbon dioxide in the reaction solvent was thoroughly investigated. It was surprising to find a sudden rise of yield of the carboxylic acids aimed at when the concentration of carbon dioxide was increased above a certain level. Namely, when the concentration of carbon dioxide was increased to 0.3 mol/l or more, carboxylic acids aimed at could be produced with a high yield. Thus, it was made clear that increase in the concentration of carbon dioxide improved conversion rate unexpectedly as well as selection rate. Thus it is assumed that the increase of the concentration of carbon dioxide not only produces a favorable effect based on the chemical reaction kinetics, that is attained by increasing the concentration of a reactant involved in one reaction of competing reactions, but also produces some change in physical properties such as polarity or basicity of the whole reaction system, with the result that stability of a reaction intermediate is increased and thus the producing rate thereof is increased, although the reason why such effects are obtained by increasing the concentration of carbon dioxide is not clear.

In short, the present invention relates to a process for producing, from a fluorine-containing aliphatic halogen compound having a general formula (I), a fluorine-containing aliphatic carboxylic acids having a general formula (II) by the reaction of (I) with carbon dioxide under the presence of zinc in an organic solvent followed by hydrolysis of the reaction product,

 (I)

 (II)

where, in the formula (I) and (II), X and X' independently denote a fluorine, chlorine, bromine, or iodine atom, but X and X' do not represent fluorine atoms at the same time, Y and Y' are carboxyl groups which substitute and combine at the combining site of X and X' in (I), and $R_f$ is a saturated or unsaturated fluorine-containing aliphatic group of a straight or branched chain which contains 1 to 20 carbon atoms when either X or X' is a fluorine atom while otherwise $R_f$ contains 3 to 20 carbon atoms, and when X or X' is a fluorine atom, the corresponding Y or Y' is also a fluorine atom, wherein the improvement comprises controlling the concentration of carbon dioxide in an organic solvent at a level of 0.3 to 5 mol/l.

DETAILED DESCRIPTION OF THE INVENTION

Hereinbelow the present invention will be described in detail.

We can show various kinds of fluorine-containing aliphatic halogen compounds which are expressed by the general formula (I) and used for the process of this invention. They include perfluoroalkylhalogen compounds of straight or branched chain, for example, $CF_3(CF_2)_pX$, $(CF_3)_2CF(CF_2)_pX$, or

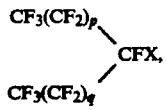

and those of which some fluorine atoms in the molecular chain are substituted by hydrogen atoms such as, for example, $CF_3CH_2CF_2X$, $HCF_2(CF_2)_pX$ or $CF_3(CF_2)_pCH_2X$, where X denotes chlorine, bromine or iodine atom, and p and q express zero or a positive integer.

Further, $R_f$, a fluorine-containing aliphatic group, in the general formula (I) may contain unsaturated bond such as a double bond between two carbon atoms, and represent a perfluoro substance or that of which a part of fluorine atoms is substituted by hydrogen atoms.

We can demonstrate the following substances which belong to the above-mentioned category: $CF_2=CF(CF_2)_pX$,

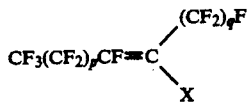

and $F_2C=CHX$, $H(F)C=C(F)X$, $H(F)C=C(H)X$, $H_2C=C(F)X$ where X, p and q have the same meaning as above.

$F_2C=C(R)X$, $F(R)C=C(F)X$, $H(R)C=C(F)X$
$F(R)C=C(H)X$, $H(F)C=C(R)X$, $H(R_f)C=C(F)X$
$F(R_f)C=C(H)X$, $H(F)C=C(R_f)X$, $H_2C=C(R_f)X$
$R_2C=C(F)X$, $R_f(R)C=C(F)X$, $R_{f2}C=C(H)X$
$R_f(R)C=C(H)X$, $F(R)C=C(R)X$, $R_f(F)C=C(R_f)X$
$R_{f2}C=C(R_f)X$, $R_f(R)C=C(R)X$, $R_2C=C(R_f)X$
$R_{f2}C=C(R)X$, $R_f(R)C=C(R_f)X$, $R(F)C=C(R_f)X$
$R_f(F)C=C(R)X$, $R_f(H)C=C(R_f)X$, $R_f(H)C=C(R)X$
$R(H)C=C(R_f)X$ where R is an alkyl group, $R_f$ is a fluorine-containing alkyl group and X is the same as above.

In addition, perfluorodihalogen compounds having a straight or branched chain expressed by the following formulae:

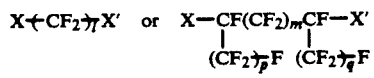

and dihalogen compounds in which fluorine atoms in the fluoroalkyl chain are partly substituted by hydrogen atoms expressed by the following formula:

are also employed for the object of this invention, where X and X' denote chlorine, bromine, or iodine atoms independently, l is an integer 3 or more, m is an integer 1 or more, and p and q have the same meaning as above.

Furthermore, fluorodihalogen compounds of which $R_f$ group in the general formula (I) has unsaturated bond such as the double bond between two carbon atoms are also employed for the object of this invention. These compounds may be cited as follows:

and

where X, X', p, and q have the same meaning as above.

Thus, a number of substances can be used as fluorine-containing aliphatic halogen compounds expressed by the general formula (I), but the number of carbon atoms constituting the fluorine-containing aliphatic group is preferably equal or less than 20 to maintain a practically high solubility of the compound in the solvent for reaction.

It is required in the reaction of the present invention that the concentration of carbon dioxide in the organic solvent be equal or greater than 0.3 mol/l. If the concentration is less than the level, the high yield this invention aims at can not be attained.

The upper limit of the concentration of carbon dioxide may be set practically at 5 mol/l, because the effect to improve the yield is remarkably diminished at a higher level. Usually, concentration of carbon dioxide in an organic solvent changes according to the nature of solvent and the temperature. Therefore, the mentioned concentration can be obtained by selecting the solvent or the temperature at which the reaction takes place. For more convenience, the desired concentration can be realized using a pressure applying apparatus such as an autoclave to raise the carbon dioxide pressure at a level higher than the normal pressure. This can be done irrespective of the solvent and the temperature of reaction. For example, when dimethylsulfoxide (hereinafter designated as DMSO) is used, concentration of carbon dioxide at 0° C. and under the normal pressure is 0.13 mol/l, but when the pressure is increased to 5 kg/cm² (absolute pressure) with a pressure applying apparatus the concentration can be increased to 0.6 mol/l (at 35° C.). If dimethylformamide (hereinafter called DMF) is used, the carbon dioxide concentration which is 0.23 mol/l at 20° C. and under the normal pressure can be increased using a pressure apparatus to 5 kg/cm² (absolute pressure to 0.85 mol/l at 35° C.

Zinc to be used in the process of above reactions should preferably be in the powdery form of which the mean diameter of particles be in the range from 0.1 to 100 μm. If the particle size is smaller than 0.1 μm in diameter, the particles are hardly removed when the reaction is completed, while the yield of reaction is decreased for the size larger than 100 μm in diameter. Thus, the mean diameter of particles is particularly preferred to be 1–50 μm from the standpoint of the yield of reaction and the easy operation.

Commerical zinc may be used without any pretreatment, but a smaller amount of the metal suffices for the purpose if it is surface-treated beforehand. For the surface treatment, the method described in HorbenWeyl, 13(2a), p.570–p.574, and p.815 may be applied. Namely the metal is treated beforehand with a mineral or acetic acid, for example, or by forming a metal couple with another metal such as copper, lead, cadmium, and mercury for ordinary cases.

Suitable amount of the zinc powder may be at least in an amount equivalent to halogen atoms other than fluorine atoms in the fluorine-containing aliphatic halogen compounds in the raw material. If the amount of zinc powder is less than an equivalent amount to the halogen atoms, the yield is naturally lowered and also reproducibility of the yield is lost for the product carboxylic acids. On the contrary, when the amount of zinc is too much, for example 10 times as much in equivalent, only a small increased effect can be expected. Thus, it is recommended to use zinc powder in an amount 1 to 10 times as much as the halogen atoms other than fluorine atom in the fluorine-containing aliphatic halogen compounds as raw material. More preferably the amount should be 2 to 10 times as much in equivalent.

The most preferred solvents to be used in the present invention are aprotic polar solvents. They include, for example, DMF, DMSO, N, N-dimethylacetamide, tetramethylurea, hexamethylphosphoramide, sulforane, N-methylpyrrolidone, nitrobenzene, nitromethane, acetonitrile, propylene carbonate, tetrahydrofurane, dioxane, ether, diglyme, triglyme and pyridine. Among them, more preferred from the reaction yield are DMF, DMSO, N-methylpyrrolidone, N, N-dimethylacetamide, tetramethylurea and hexamethylphosphoramide.

The reaction of this invention can take place in a wide range of temperature, but in ordinary cases a temperature range 0° to 150° C., preferably 0° to 100° C., is selected. At a temperature below 0° C. the process is not practical, because the raw material halogen compounds require a very long reaction time to obtain a high conversion rate, though carbon dioxide in the solvent can easily be maintained at a high concentration. On the other hand, if the temperature exceeds 150° C., a high pressure is needed to maintain a predetermined high concentration of carbon dioxide in the solvent and, in addition, the increased rate of side reactions decreases the selection rate to the route to the carboxylic acids aimed at.

The reaction of fluorine-containing aliphatic halogen compound is proceeded in an organic solvent in the presence of suspended zinc by contact with carbon dioxide at a predetermined temperature. Since the concentration of carbon dioxide in the reaction solvent is important in the present invention, the concentration must be maintained throughout the reaction at a value not lower than 0.3 mol/l. For this end, the concentration of carbon dioxide is either set up initially at a value high enough not to fall below 0.3 mol/l throughout the reaction, or supplied continually to compensate the consumed amount. The raw material halogen compound should preferably be added continually to a mixture of the reaction solvent and zinc which is kept at a predetermined temperature and contains carbon dioxide at a predetermined concentration.

The more slowly the raw material halogen compound is added, the better is the yield of the final product. But the most preferred speed is in the range from 0.05 to 10 mol/hr per liter of solvent. A speed below 0.05 mol/hr is not practial because it takes too long a time for the addition. On the contrary, an adding speed exceeding 10 mol/hr gives rise to a remarkable decrease of the yield. When the addition is made, the reaction time will be 30 min to 48 hr after the completion of addition of fluorine-containing aliphatic halogen compound.

However, if the raw material halogen compound is in the form of solid and is not so soluble to the reaction solvent as to adopt the addition method as mentioned above, it is also possible to proceed the reaction by adding the solvent to a mixture of said halogen compound and zinc under the atmosphere of carbon dioxide. In this case, 30 min to 48 hr suffice for the reaction after the addition of the solvent and the establishment of the reaction temperature.

Thus, fluorine-containing aliphatic halogen compound is allowed to react with carbon dioxide in the presence of zinc, and the product is hydrolyzed to obtain the aimed fluorine-containing aliphatic carboxylic acid. The hydrolysis is readily conducted by mere contact with a mineral acid such as hydrochloric, sulfuric and nitric.

The process of the present invention is very useful to convert fluorine-containing aliphatic halogen compounds into fluorine-containing aliphatic carboxylic acids with a high yield without producing a least amount of by-products. Consequently, in addition, the operation to recover unreacting raw material will probably be unnecessary, the object product will be purified in a simpler process and can be isolated more readily. Thus, the process is very useful for the industrial purposes.

EXAMPLES

The present invention will be described more in detail by referring to Examples and Comparison Examples hereinbelow, but it should be understood the invention is not limited thereto.

EXAMPLE 1

Into an electromagnetic agitation autoclave of 200 cc capacity which was provided with an inlet for carbon dioxide gas and a pressure inlet for perfluoroalkyl iodide, 19.6 g (or 0.3 gram atom) of zinc dust (having 15 μm mean particle diameter) which had been washed beforehand with 0.5N hydrochloric acid and dried was added and the inside of the autoclave was heated to 35° C. by the outer heating. The pressure of carbon dioxide was made 6.0 kg/cm² (absolute pressure) with a constant pressure device. The pressure was kept at the constant value throughout the treatment. Then 80 ml of DMF was pumped to the autoclave under stirring by a liquid delivery pump. The DMF, as soon as it was transferred to the autoclave, began to dissolve carbon dioxide and finally reached a saturation concentration (1.0 mol/l) at the carbon dioxide pressure (6.0 kg/cm², absolute pressure) in the gaseous phase. Then a mixture of 54.6 g (or 0.1 mol) of perfluorooctyl iodide and 3 ml of DMF was transferred into the autoclave under pressure with the liquid delivery pump in an hour and 15 min at a constant speed. Agitation was continued for 2 hr and 45 min at the same temperature. Then the pressure of carbon dioxide in the autoclave was released to the atmospheric pressure to terminate the reaction.

The excess of zinc (13 g) was removed by filtration from the reaction mixture and the solvent DMF was partly removed by distillation, to concentrate the filtrate. This concentrate was poured into a 6N aqueous hydrochloric acid to hydrolyze the reaction intermediate. Concentrated sulfuric acid was added and the mixture was distilled, to obtain 42.7 g of $C_8F_{17}COOH$.

A yield of 92% was obtained. The product melted at 70°–71° C. and boiled at 107° C./17 mmHg.

EXAMPLES 2–7 AND COMPARISON EXAMPLE 1

The pressure of carbon dioxide and the reaction temperature was set up as shown in Table 1. The process was the same as in Example 1, except that the carbon dioxide concentration in DMF was varied. In Comparison Example, carbon dioxide was kept at the normal pressure and the concentration of carbon dioxide in DMF was 0.20 mol/l. Results are shown in Table 1.

TABLE 1

| | Temperature of reaction (°C.) | Pressure of $CO_2$ (abs.kg/cm²) | Concentration of $CO_2$ (mol/l) | Yield (%) |
|---|---|---|---|---|
| Example 2 | 35 | 2.0 | 0.35 | 86 |
| Example 3 | 35 | 3.5 | 0.60 | 90 |
| Example 4 | 60 | 6.0 | 0.73 | 91 |
| Example 5 | 15 | 6.0 | 1.40 | 94 |
| Example 6 | 25 | 6.0 | 1.25 | 94 |
| Example 7 | 35 | 11.0 | 1.90 | 96 |
| Comparison Example 1 | 25 | Normal Pressure | 0.20 | 72 |

COMPARISON EXAMPLE 2

A mixed gas of carbon dioxide and nitrogen (of which carbon dioxide was 16.7 vol %) was made 6 kg/cm². Other conditions were the same as in Example 1. The concentration of carbon dioxide in DMF was 0.16 mol/l. $C_8F_{17}COOH$ was obtained with a yield of 68%.

EXAMPLE 8

The procedure was the same as in Example 1, except that the amount of zinc employed was 7.85 g (or 0.12 gram atom) instead of 19.6 g (or 0.3 gram atom). As a result, the yield of $C_8F_{17}COOH$ was 80%.

EXAMPLE 9

The procedure was the same as in Example 1, except that the amount of zinc employed was 39.2 g (or 0.6 gram atom) instead of 19.6 g (or 0.3 gram atom). As a result, the yield of $C_8F_{17}COOH$ was 93%.

EXAMPLES 10–12

The procedure was the same as in Example 1, except that the solvents indicated in Table 2 were used in place of DMF. Results are shown in Table 2.

TABLE 2

| Example | Solvent | Pressure of $CO_2$ (abs. kg/cm²) | Concentration of $CO_2$ (mol/l) | Yield (%) |
|---|---|---|---|---|
| 10 | N-Methylpyrrolidone | 6.0 | 0.8 | 87 |
| 11 | N,N-dimethylacetamide | 6.0 | 0.9 | 88 |
| 12 | Dimethylsulfoxide | 6.0 | 0.7 | 82 |

EXAMPLE 13

The same procedure as in Example 1 was followed except that 23.0 g (or 0.35 gram atom, 15 μm mean particle size in diameter) of commercially available zinc was employed. $C_8F_{17}COOH$ was obtained with a yield of 92%.

EXAMPLE 14

The same procedure as in Example 1 was followed except that 44.6 g (or 0.1 mol) of perfluorohexyl iodide was employed in place of 54.6 g (or 0.1 mol) of perfluorooctyl iodide and the reaction was conducted at 25° C. 33.5 g of $C_6F_{13}COOH$ was obtained with a yield of 92%. The product melted at 25°–26° C. and boiled at 72° C./20 mmHg.

EXAMPLE 15

Into a 200 cc electromagnetic agitation type autoclave provided with an inlet for carbon dioxide, 13.0 g (or 0.020 mol) of perfluorodecyl iodide and 4.0 g (or 0.061 gram atom) of zinc powder (15 μm mean particle size in diameter) were introduced. The temperature in the inside of the autoclave was cooled to 5° C. by the outer cooling. Carbon dioxide was introduced via a constant pressure device to attain a pressure of 4 kg/cm² (absolute pressure). While the content of the autoclave was being agitated, 80 ml of DMF at the same temperature was introduced in 30 min.

The temperature inside the autoclave was elevated to 35° C. by the outer heating and agitation started. Pressure inside the autoclave was elevated to 5.7 kg/cm² which was maintained to the completion of the reaction. At this moment, concentration of carbon dioxide in DMF was 0.95 mol/l in the autoclave. Starting the reaction with stirring at 35° C., the pressure in the autoclave was released to terminate the reaction after 5 hours.

Excess of zinc in the reaction mixture was removed by filtration and the solvent DMF was partly removed by distillation to concentrate the filtrate. Subsequently this concentrate was poured into 6N aqueous hydrochloric acid to hydrolyze the reaction intermediate. Further, the product was extracted with diethylether. To the ether solution, a diazomethane solution in ether was added to convert the product $C_{10}F_{21}COOH$ into methyl ester and the reaction yield was estimated by the gas chromatography using an internal standard. Results showed a yield of 92% for the production of $C_{10}F_{21}COOH$.

EXAMPLE 16

Into a 200 cc electromagnetic agitation type autoclave provided with an inlet for carbon dioxide and a pressure inlet for 3, 3, 3-trifluoro-2-iodopropene was placed 19.6 g (or 0.3 gram atom) of zinc dust (15 μm mean particle size in diameter) which had been washed with 0.5N aqueous hydrochloric acid and dried. The inside of autoclave was heated to 35° C. by the outer heating. The pressure of carbon dioxide was elevated to 6.0 kg/cm² (absolute pressure) with a constant pressure device and the pressure of carbon dioxide in the autoclave was maintained throughout the reaction period. Then 80 ml of DMF was introduced to the autoclave with a liquid delivery pump under agitation. The DMF, as soon as it was introduced in the autoclave, began to dissolve carbon dioxide, at last to reach the saturation concentration (1 mol/l) under gaseous carbon dioxide phase pressure 6.0 kg/cm² (absolute pressure).

Then a mixture of 22.2 g (or 0.10 mol) of 3, 3, 3-trifluoro-2-iodopropene and 10 ml of DMF was introduced under pressure into the autoclave in 1 hour. Stirring was continued for additional 2 hours at the same temperature and then the pressure in the autoclave was released to the normal pressure to terminate the reaction.

From the reaction mixture, excessive 13 g of zinc was removed by filtration and the solvent DMF was partly removed and recovered by distillation to concentrate the filtrate. The concentrate was poured in a 6N aqueous hydrochloric acid to hydrolyze the reaction intermediate. Then followed were the extraction with diethylether and drying of the extract. By distilling the ether 11.5 g of α-trifluoromethylacrylic acid was obtained (82% of yield). The product was identified by comparing spectroscopic data with those of standard substance in GLC, IR and NMR.

EXAMPLES 17-19

The carbon dioxide pressure and the reaction temperature were set up as shown in Table 3. Procedure was the same as that in Example 16 except that the concentration of carbon dioxide in DMF was varied. Results are shown in Table 3.

TABLE 3

| Example | Temperature of reaction (°C.) | Pressure of $CO_2$ (abs. kg/cm²) | Concentration of $CO_2$ (mol/l) | Yield (%) |
|---------|-------------------------------|----------------------------------|----------------------------------|-----------|
| 17 | 35 | 2.0 | 0.35 | 76 |
| 18 | 60 | 11.0 | 1.35 | 84 |
| 19 | 35 | 11.0 | 1.90 | 85 |

EXAMPLE 20-22:

The procedure was the same as in Example 16, except that the solvents indicated in Table 4 were used in place of DMF. Results are shown in Table 4.

TABLE 4

| Example | Solvent | Pressure of $CO_2$ (abs. kg/cm²) | Concentration of $CO_2$ (mol/l) | Yield (%) |
|---------|---------|----------------------------------|----------------------------------|-----------|
| 20 | N-Methyl-pyrrolidone | 6.0 | 0.8 | 75 |
| 21 | N.N-Dimethyl-acetamide | 6.0 | 0.9 | 78 |
| 22 | Dimethyl-sulfoxide | 6.0 | 0.7 | 76 |

EXAMPLE 23

The procedure employed in this example was the same as in Example 16, except that 17.5 g (or 0.1 mol) of 3, 3, 3-trifluoro-2-bromopropene ($CF_3BrC=CH_2$) was used in place of 3, 3, 3-trifluoro-2-iodopropene and the mixture after said bromine compound was added was agitated for 24 hours. 8.4 g of α-trifluoromethylacrylic acid was obtained with a yield of 60%.

EXAMPLE 24

The same procedure as that of Example 16 was employed, except that 23.0 g (or 0.35 gram atom) of commercial zinc (15 μm mean particle diameter) was used without any pretreatment. With a yield of 80%, α-trifluoromethylacrylic acid was obtained.

EXAMPLE 25

To a mixed solution of 50 ml of DMF and 10 ml of acetic acid, was added 0.6 g of copper acetate and the mixture was heated at 40°-50° C. Then 19.6 g (or 0.3 gram atom) of commercial zinc powder was added to the mixture and agitated for 30 min. After cooled, the mixture was washed 4 times with 25 ml of DMF to obtain zinc-copper couple.

The same procedure was followed as in Example 16, except that the zinc-copper couple was used. As a result, α-trifluoromethylacrylic acid was obtained with a yield of 80%.

EXAMPLES 26-29

The same procedure as that in Example 16 was followed, except that, in place of 3, 3, 3-trifluoro-2-iodopropene, each 0.10 mol of 3, 3, 4, 4, 5, 5, 6, 6, 6-nonafluoro-2-iodohexene, 1, 2, 2-trifluoro-1-iodoethene, 1, 2-difluoro-1-iodo-3-methylpentene or 2, 3, 3, 4, 4, 5, 5, 6, 6, 7, 7, 8, 8, 9, 9, 9-hexadecafluoro-1-iodononene was employed. Corresponding α, β-unsaturated carboxylic acids were obtained. Each product was identified by IR and NMR. Results are shown in Table 5.

TABLE 5

| Example | Product | Yield (%) |
|---------|---------|-----------|
| 26 | n-$C_4F_9C(CO_2H)=CH_2$ | 65 |
| 27 | $CF_2=CFCO_2H$ | 80 |
| 28 | $CH_3CH_2CH(CH_2)CF=CFCO_2H$ | 74 |
| 29 | n-$C_7F_{15}CF=CHCO_2H$ | 71 |

COMPARISON EXAMPLE 3

To a 300 ml 4-necked flask provided with an inlet tube for introducing carbon dioxide, dropping funnel, reflux cooler (of which coolant was dry ice-acetone) and a stirrer, were added 19.6 g (or 0.3 gram atom) of zinc powder (15 μm mean particle diameter) which had been washed with 0.5N aqueous hydrochloric acid and then dried and 80 ml of DMF. Carbon dioxide gas was introduced in a speed of 45 ml/min for 30 min under the normal pressure (Temperature was 25° C., and the concentration of carbon dioxide in DMF was about 0.2 mol/l). Subsequently, while carbon dioxide being introduced at the same flow rate at 25° C., a mixture of 22.2 g (or 0.1 mol) of 2-iodo-3, 3, 3-trifluoropropene and 10 ml of DMF was added in drops in an hour through the dropping funnel. Agitation was continued at the same temperature for additional 4 hours. Then excess of zinc was removed from the reaction mixture and 5.6 g of α-trifluoromethylacrylic acid (40% yield) was obtained in the same process as described in Example 16.

COMPARISON EXAMPLE 4

The same procedure as that in Example 16 was followed, except that the pressure 6 kg/cm$^2$ in the inside of autoclave was produced with a mixed gas of carbon dioxide and nitrogen (carbon dioxide occupied 16.7 vol %) instead of carbon dioxide alone Concentration of carbon dioxide in DMF was 0.16 mol/l. Yield of α-trifluoromethylacrylic acid was 42%.

EXAMPLE 30

The same procedure as that in Example 16 was followed, except that the amount of zinc was changed from 19.6 g (or 0.3 gram atom) to 7.85 g (or 0.12 gram atom). Yield of α-trifluoromethylacrylic acid was 57%.

EXAMPLE 31

The same procedure as that in Example 16 was followed, except that the amount of zinc was changed from 19.6 g (or 0.3 gram atom) to 39.2 g (or 0.6 gram atom) Yield of α-trifluoromethylacrylic acid was 85%.

EXAMPLE 32

Into a 200 cc electromagnetic agitation type autoclave provided with an inlet for carbon dioxide and a pressure inlet for perfluoroalkyl diiodide, was placed 19.6 g (or 0.3 gram atom) of zinc dust (15 μm mean particle size in diameter) which had been washed with 0.5N aqueous hydrochloric acid and dried. The inside of autoclave was heated to 35° C. by the outer heating. The pressure of carbon dioxide was elevated to 6.0 kg/cm$^2$ (absolute pressure) with a constant pressure device and the pressure of carbon dioxide in the autoclave was maintained throughout the reaction period. Then 80 ml of DMF was introduced to the autoclave with a liquid delivery pump under agitation. The DMF, as soon as it was introduced in the autoclave, began to dissolve carbon dioxide, at last to reach the saturation concentration (1 mol/l) under gaseous carbon dioxide phase pressure 6.0 kg/cm$^2$ (absolute pressure).

Then a mixture of 22.7 g (or 0.05 mol) of 1, 4-diiodoperfluorobutane and 10 ml of DMF was introduced under pressure into the autoclave in 1 hour. Stirring was continued for additional 1 hour at the same temperature and then the pressure in the autoclave was released to the normal pressure to terminate the reaction.

From the reaction mixture, excessive 13 g of zinc was removed by filtration and the solvent DMF was partly removed and recovered by distillation to concentrate the filtrate. The concentrate was poured in a 6N aqueous hydrochloric acid to hydrolyze the reaction intermediate. Then followed the extraction with diethylether, drying of the extract and the methyl esterification with diazomethane. The yield of perfluoroadipic acid as estimated by gas chromatography was 88%. The perfluroadipic acid and the dimethyl esters thereof were identified by $^1$R, $^1$HNMR, and $^{19}$F-NMR.

EXAMPLES 33–35

The same procedure as that in Example 32 was followed, except that the pressure of carbon dioxide and the temperature of reaction were set up as indicated in Table 6 and the concentration of carbon dioxide in DMF was varied. Results are shown in Table 6.

TABLE 6

| Example | Temperature of reaction (°C.) | Pressure of CO$_2$ (abs. kg/cm$^2$) | Concentration of CO$_2$ (mol/l) | Yield (%) |
|---|---|---|---|---|
| 33 | 35 | 2.0 | 0.35 | 82 |
| 34 | 15 | 6.0 | 1.40 | 90 |
| 35 | 35 | 11.0 | 1.90 | 93 |

EXAMPLES 36–38

The same procedure as that in Example 32 was followed, except that the solvents indicated in Table 7 were employed in place of DMF. Results are shown in Table 7.

TABLE 7

| Example | Solvent | Pressure of CO$_2$ (abs. kg/cm$^2$) | Concentration of CO$_2$ (mol/l) | Yield (%) |
|---|---|---|---|---|
| 36 | N-Methylpyrrolidone | 6.0 | 0.8 | 85 |
| 37 | N,N-Dimethylacetamide | 6.0 | 0.9 | 87 |
| 38 | Dimethylsulfoxide | 6.0 | 0.7 | 80 |

EXAMPLE 39

The same procedure as that in Example 32 was employed, except that 1, 6-diiodoperfluorohexane was used as a perfluoroalkyldihalogen compound in an amount of 27.7 g (or 0.05 mol). The perfluorosuberic acid (HO$_2$C(CF$_2$)$_6$CO$_2$H) was obtained with a yield of 85%. The product was identified by 1R, $^{19}$F-NMR and $^1$H-NMR.

EXAMPLE 40

The same procedure as that in Example 32 was followed, except that 23.0 g (or 0.35 gram atom) of commercial zinc (15 μm mean particle diameter) which was not surface treated was used. Perfluoroadipic acid was obtained with a yield of 84%.

EXAMPLE 41

To a mixed solution of 50 ml of DMF and 10 ml of acetic acid, was added 0.6 g of copper acetate and the mixture was heated at 40°–50° C. Then 19.6 g (or 0.3 gram atom) of commercial zinc powder was added to the mixture and agitated for 30 min. After cooled, the mixture was washed 4 times with 25 ml of DMF to obtain zinc-copper couple.

The same procedure was followed as in Example 32, except that the zinc-copper couple was used. As a result, perfluoroadipic acid was obtained with a yield of 86%.

EXAMPLE 42

The same procedure as that in Example 32 was followed, except that, as perfluoroalkyl dihalogen compound, 1,6-dibromoperfluorohexane was used in an amount of 23 g (or 0.05 mol). Perfluorosuberic acid was obtained with a yield of 75%.

COMPARISON EXAMPLE 5

To a 300 ml 4-necked flask provided with an inlet tube for introducing carbon dioxide, dropping funnel, reflux cooler and a stirrer, were added 19.6 g (or 0.3 gram atom) of zinc powder (15 μm mean particle diameter) which had been washed with 0.5N aqueous hydrochloric acid and then dried and 80 ml of DMF. Carbon dioxide gas was introduced in a speed of 45 ml/min for 30 min under the normal pressure (Temperature was 25° C., and the concentration of carbon dioxide in DMF was about 0.2 mol/l). Subsequently, while carbon dioxide being introduced at the same flow rate at 25° C., a mixture of 22.7 g of 1,4-diiodoperfluorobutane and 10 ml of DMF was added in drops in an hour through the dropping funnel. Agitation was continued at the same temperature for additional 2 hours. Then excess of zinc was removed from the reaction mixture and perfluoroadipic acid was produced in the same process as described in Example 32. The yield estimated to be 45%.

COMPARISON EXAMPLE 6

The Example for comparison was carried out in the same procedure as in Comparison Example 5, except that the zinc dust in Comparison Example 5 was replaced by the zinc-copper couple prepared in a process similar to that in Example 41. Yield of perfluoroadipic acid was 54%.

COMPARISON EXAMPLE 7

The same procedure as that in Example 32 was followed, except that the pressure 6 kg/cm² in the inside of autoclave was produced with a mixed gas of carbon dioxide and nitrogen (carbon dioxide occupied 16.7 vol %) instead of carbon dioxide alone. Concentration of carbon dioxide in DMF was 0.16 mol/l. Yield of perfluoroadipic acid was 50%.

EXAMPLE 43

The same procedure as that in Example 32 was followed, except that the amount of zinc employed was changed from 19.6 g (or 0.3 gram atom) to 7.85 g (or 0.12 gram atom). The yield of perfluoroadipic acid was 65%.

EXAMPLE 44

The same procedure as that in Example 32 was followed, except that the amount of zinc employed was changed from 19.6 g (or 0.3 gram atom) to 30.2 g (or 0.6 gram atom). The yield of perfluoroadipic acid was 90%.

What is claimed is:

1. A process for producing a fluorine-containing aliphatic carboxylic acid having general formula (II) from a fluorine-containing aliphatic halogen compound having general formula (I) which process comprises the reaction of (I) at from 0°–100° C. with carbon dioxide in the presence of 1–10 equivalents of powdered zinc per equivalent of atoms of halogen other than fluorine in (I) in an organic solvent selected from the group consisting of dimethyl formamide, N-methylpyrrolidone, N,N-dimethylacetamide and dimethylsulfoxide followed by hydrolysis of the reaction product:

$$X-R_f-X' \quad (I)$$

$$Y-R_f-Y' \quad (II)$$

where, in formulae (I) and (II), X and X' independently denote a fluorine, chlorine, bromine or iodine atom, but X and X' do not both represent fluorine atoms at the same time, Y and Y' are carboxyl groups which substitute and combine at the combining site of X and X' in (I), and $R_f$ is a saturated or unsaturated fluorine-containing straight or branched chain aliphatic group which contains 1 to 20 carbon atoms when either X or X' is a fluorine atom while otherwise $R_f$ contains 3 to 20 carbon atoms, and when X or X' is a fluorine atom, the corresponding Y or Y' is also a fluorine atom, which process involves controlling the concentration of carbon dioxide in the organic solvent at a level of 0.3 to 5 mol/l.

* * * * *